United States Patent [19]

Gries et al.

[11] Patent Number: 5,098,692
[45] Date of Patent: Mar. 24, 1992

[54] CALCIUM CHELATE AND GADOLINIUM PHARMACEUTICAL COMPOSITION AND METHODS OF X-RAY AND NMR IMAGING

[75] Inventors: Heinz Gries; Ulrich Speck; Hanns-Joachim Weinmann; Hans P. Niendorf; Wolfgang Seifert, all of Berlin, Fed. Rep. of Germany

[73] Assignee: Schering Aktiengellschaft, Berlin and Bergkamen, Fed. Rep. of Germany

[21] Appl. No.: 601,594

[22] Filed: Oct. 22, 1990

Related U.S. Application Data

[63] Continuation of Ser. No. 126,099, Nov. 30, 1987, abandoned.

[30] Foreign Application Priority Data

Nov. 28, 1986 [DE] Fed. Rep. of Germany ....... 3640708

[51] Int. Cl.$^5$ .................... A61K 49/04; A61K 49/00
[52] U.S. Cl. ........................................... 424/9; 424/4; 424/5
[58] Field of Search .................... 424/5, 4, 9

[56] References Cited

U.S. PATENT DOCUMENTS

| | | | |
|---|---|---|---|
| 3,033,757 | 5/1962 | Hallett | 424/5 |
| 3,175,952 | 3/1965 | Bird | 424/5 |
| 4,247,534 | 1/1981 | Bevan | 424/1 |
| 4,432,963 | 2/1984 | Bevan | 424/1.1 |
| 4,478,816 | 10/1984 | Ledley et al. | 424/4 |
| 4,647,447 | 3/1984 | Gries et al. | 424/9 |
| 4,746,507 | 5/1988 | Quag | 424/9 |

FOREIGN PATENT DOCUMENTS

| | | | |
|---|---|---|---|
| 0169299 | 1/1986 | European Pat. Off. | 424/9 |
| 0173163 | 3/1986 | France | 424/9 |
| 4311288 | 5/1969 | Japan | 424/4 |
| WO90/03804 | 4/1990 | PCT Int'l Appl. | |

OTHER PUBLICATIONS

Skucas et al., Radiographic Contrast Agents, "Urography" Spataro, 245-251 (1989).
Contrast Media, Carr, "Mechanisms of Adverse Reactions," Dawson, 14-15 (1988).
Contrast Media: Biol. Effects & Clin. Appln., vol. I (1989) Parvez Ed., Ch 4, "Newer Perspectives in C M Chem.", Speck 47 & 63.
Owitt et al., Improved Instrumentation Etc., NTIS No. PB 82-118688, 9/1/79, pp. 1, 2, 68-167.
Owitt et al., Improved Instrumentation Etc., NTIS No. PB 272617, May, 1977, pp. 1, 2, 69, 70.
Papio et al., Circulation, 58, #3, 9;78, 520-528.
Speck et al., Radiology Today, 3, Ed. Donner et al., Springer Verlag, 1985, 180-183.

Primary Examiner—Frederick E. Waddell
Assistant Examiner—Gregory Hook
Attorney, Agent, or Firm—Millen, White & Zelano

[57] ABSTRACT

Improved metal complex-containing pharmaceutical agents are described which, as an additive, contain one or more complexing agents and/or one or more weak metal complex(es) or mixtures thereof.

25 Claims, No Drawings

CALCIUM CHELATE AND GADOLINIUM PHARMACEUTICAL COMPOSITION AND METHODS OF X-RAY AND NMR IMAGING

This application is a continuation of application Ser. No. 07/126,099, filed Nov. 30, 1987, now abandoned.

BACKGROUND OF THE INVENTION

This invention relates, e.g., to improved agents based on metal-containing complex compounds suitable for NMR, X-ray, ultrasound and radiodiagnosis and therapy and a process for their production.

Soon after the discovery of X-rays the most varied substances were experimentally tested as "contrast media" to boost the insufficient contrast of body fluids and soft tissues (Barke, R. Roentgenkontrastmittel [X-ray Contrast Media]; Chemie, Physiologie, Klinik VEB Georg Thieme Leipzig, 1970). Heavy elements were suitable as the X-ray absorbing elements of such contrast media. In the course of a long selection and optimization process, finally only contrast media based on iodine (in a stable organic bond) or barium (as a nearly insoluble sulfate) remained. Barium sulfate is used exclusively for visualization of the gastro-intestinal tract and it does not penetrate the body.

With the development of nuclear medicine, e.g., the use of radioactive elements for visualizing certain structures of the organism and pathological areas and especially for functional diagnosis and for radiotherapy, a series of other metals was accepted for in vivo diagnosis. The so-called radiopharmaceuticals used in nuclear medicine contain either a radioactive isotope of iodine ($^{131}$I or $^{123}$I) or preferably a meta such as $^{99m}$technetium. These elements are bonded to an organic substance in many cases or, in the case of the radioactive metal isotope, are administered in complexed form. Most often, the stability of the complexing of the metals is such that, during its stay in the body, a more or less large portion of the metal cannot be prevented from being released from its bond to the organic molecule. Thus, in general, the metal ion loses its desired pharmacokinetic and diagnostic properties produced by the complexing, is eliminated only very slowly, disturbs the distribution picture, specific in itself, of the isotope that is still bonded and can exhibit its inherently toxic properties.

At the beginning of the 1980s the interest in metal complexes in diagnostics and therapy increased further. With the development of nuclear spin tomography there arose the question of producing contrast, e.g., signal-influencing substances that could be introduced into the body from the outside. Such substances help to recognize diseases earlier and more accurately. As an effective principle, complex paramagnetic metal ions were introduced which, despite a relatively high dosage (e.g., several grams of complex that contain about 1-2 g of heavy metal) and rapid intravenous injection, have proven to be surprisingly well tolerated (R. Felix, W. Schoerner, M. Laniado, H.P. Niendorf, C. Claussen, W. Fiegler, U. Speck; Radiology 156, 3: 681–688 (1985)). Especially notable is the obviously outstanding acute tolerance of gadolinium-DTPA (European patent application 71564), the most advanced preparation to date in clinical use. The extremely low number and the mild nature of the acute side effects caused by gadolinium-DTPA make it appear suitable also for use in connection with certain X-ray techniques. The necessity of higher dosages and of repeated administration exists for a series of diagnostic problems in nuclear spin tomography and very generally in X-ray diagnosis. In this connection, the question of long-term tolerance of substances containing heavy metals must be given great attention.

Unlike the case for iodine in the iodine-containing X-ray contrast media, the central atoms in the metal-containing complex compounds that are suitable for NMR, X-ray, ultrasound and radiodiagnosis and for therapy are not bonded covalently. The bond of the metal ion is subject to equilibrium with the surroundings which, according to nature, should be on the side of the complex as much as possible. However, a permanent bond can never be attained. In addition it should be noted that the stability constants, some very high, indicated for the complexes relate to unphysiologically high pH 15 values and do not apply for the in vivo situation. Further, in vivo, a concurrence of different ions is involved in the bond to the complexing agents so that the probability for the undesired and sometimes dangerous release of heavy metal ions in the organism increases.

The danger becomes greater
  the higher the dosage of the heavy metal complex
  the more often the complex is used
  the longer it remains in the body
  the more chemically or metabolically unstable the complexing agent is and
  the more it penetrates the cells of the body.

On the other hand, tissue-specific complexes, for example also those complexes bonded to biomolecules or macromolecules, desired for diagnosis and radiotherapy of certain types of pathological changes are precisely those, in comparison to gadolinium-DTPA, characterized by a longer and more intracellular stay in the body.

Thus, for diverse purposes, there is a need for better tolerated agents in which a release of the heavy metal ion in question from the complex compound is prevented as much as possible.

SUMMARY OF THE INVENTION

Thus, it is an object of the invention to make available such a pharmaceutical agent, as well as a process for its production.

Upon further study of the specification and appended claims, further objects and advantages of this invention will become apparent to those skilled in the art.

It has been found that adding one or more free complexing agent(s) and/or one or more weak metal complex(es) or their mixtures to pharmaceutical agents based on metal complexes surprisingly yields unobjectionably tolerable complexes.

In this connection, the complexing agent can be identical or different in all three components, i.e., in the diagnostic agent or therapeutic agent, in the additive complexing agent, and in the additive of a weaker metal complex. Suitable such complexing agents include, for example, the complexing agents disclosed in patent applications EP 71.564 (e.g., ethylenediaminetetraacetic acid EDTA, diethylenetriaminepentaacetic acid DTPA and many others), DE-OS 3401052 (e.g., 1,4,7,10-tetraazacyclododecane-N,N',N", N'''-tetraacetic acid DOTA, trans-1,2-cyclohexylenediamine-N,N,N',N'-tetraacetic acid and many others), EP 130934 (e.g., N$^6$-carboxymethyl-N$^3$,N$^9$-[2,3-dihydroxy-N-methylpropylcarbamoylmethyl ]-3,6,9-triazaundecanedioic acid and many others) and, for example, N$^6$-carboxymethyl-N$^3$, $N^9$-bis (methylcarbamoylmethyl)-3,6,9-triazaundecanedioic acid, $N^3$, $N^6$-bis(carboxymethyl)-$N^9$-3-oxapentamethylene-carbamoylmethyl-3,6,9-triazaundecanedioic acid, $N^3$, $N^6$- bis (carboxymethyl] -3,6,9-triazaundecanedioic acid, etc. Suitable complexing agents are also disclosed closed in U.S. Pat. No. 4,647,447, and U.S. Pat. Nos. 936,055 of Nov. 28, 1986, 020,992 of Mar. 2, 1987, 627,143 of July 2, 1984, 063,355 of June 18, 1987, 078,507 of July 28, 1987, 100,681 of Sept. 24, 1987, and others.

Among suitable weaker metal complexes are those that have a relatively low stability constant; preferred are those that have, as a central atom, a metal ion of elements occurring naturally in the organism such as calcium, magnesium, zinc and iron.

The additives to be used in accordance with this invention can be routinely selected by those of skill in the art in accordance with this specification. The complexing agents used as additives, as noted elsewhere, can be selected from the wide variety of complexing agents known to be useful chelating agents for metals, and especially from those disclosed as being useful in conjunction with forming metal complexes useful for the mentioned diagnostic or therapeutic procedures. The magnitude of the difference between the stability constants of the active complex and the additive complex is not critical; it is important only that the stability constant of the additive complex be lower than that of the active complex. Typically, however, the difference between the stability constants of the two complexes will be on the order of at least $10^2$.

The metal of the metal complex additive will in all cases be different from the metal of the active metal complex and, as mentioned below, most preferably will be a physiologically well-tolerated metal such as one which is natural in the organism but, in all cases, will have a biological tolerance which is greater than that of the metal per se in the active metal complex.

The complexing agents (chelating agents) and metal complexes can be used in the form of physiologically aceptable salts of inorganic (e.g., potassium, sodium, lithium hydroxide) or organic (e.g., primary, secondary, tertiary amines) such as ethanolamine, morpholine, glucamine, N-methyl, N,N-dimethylglucamine) bases, basic amino acids and amino acid amides (e.g., lysine, arginine, ornithine) or acids (e.g., glucuronic acid, acetic acid), etc., e.g., as disclosed in the documents cited above.

The production of exemplary additives is described by the following examples:

(1) Calcium-disodium salt of 1,4,7,10-tetraazacyclododecane-N,N', N'''-tetraacetic acid (DOTA)

40.40 g (0.1 mol) of DOTA (Parish Chemical Comp.) is refluxed with 10.0 g (0.1 mol) of calcium carbonate in 100 ml of water until generation of gas has ended. Then, by adding 200 ml of a 1 N sodium hydroxide solution, a neutral saline solution is produced which is evaporated to dryness in a vacuum. 50.5 g of a monohydrate is obtained as a white powder with a decomposition point above 250° C.

Analysis (relative to an anhydrous substance):
C 39.50, H 4.97, N 11.52, Ca 8.24 (calculated).
C 39.65, H 5.05, N 11.30, Ca 8.18 (found).

The zinc disodium salt of DOTA is obtained in an analogous way from DOTA, zinc carbonate and sodium hydroxide solution.

(2) $N^6$-carboxymethyl-$N^3$,$N^9$-bis(methylcarbamoylmethyl)-3,6,9-triazaundecanedioic acid 17.9 g (50 mmol) of 1,5-bis(2,6-dioxomorpholino)-3-azapentane-3-acetic acid is mixed in 50 ml of water with 100 ml of an aqueous molar solution of methylamine. It is stirred for 12 hours at room temperature and the weak, yellow solution is bleached by filtration through activated carbon. After evaporation in a vacuum, 20.5 g (=98% of the theoretical) of a white hygroscopic powder with a melting point of 78–82° C. is obtained.

Analysis (relative to an anhydrous substance):
C 45.81, H 6.97, N 16.70 (calculated).
C 45.62, H 7.03, N 16.52 (found).

(3) (a) $N^3$-(2,6-dioxomorpholinoethyl)-$N^3$-(ethoxycarbonylmethyl)-3,6-diazaoctanedioic acid.

A suspension of 21.1 g (50 mmol) of $N^3$,$N^6$-bis-(carboxymethyl)-$N^9$-(ethoxycarbonylmethyl)-3,6,9-triaza undecanedioic acid (J. Pharm. Sci. 68, 1979, 194) in 250 ml of acetic anhydride is stirred, after the addition of 50 ml of pyridine, for 3 days at room temperature. Then the precipitate is suctioned off, it is washed three times, each time with 50 ml of acetic anhydride and it is finally stirred up for several hours with absolute diethyl ether. After suctioning off, washing with absolute diethyl ether and drying in a vacuum at 40° C., 18.0 g (=89% of theory) of a white powder with a melting point of 195°–196° C. is obtained.

Analysis:
C 47.64, H 6.25, N 10.42 (calculated).
C 47.54, H 6.30, N 10.22 (found).

(b) Tetrasodium salt of $N^3$,$N^6$-bis-(carboxymethyl)-$N^9$-3-oxapentamethylene-carbamoylmethyl-3,6,9-triazaundecanedioic acid.

2.42 g (6 mmol) of the compound obtained in a) is suspended in 30 ml of dimethyl formamide. Then, at - 5° C., 3.04 g (30 mmol) of triethylamine and 0.52 ml (6 mmol) of morpholine are added, left at this temperature for 2 hours, then it is further stirred overnight, evaporated in a vacuum to dryness and the residue is mixed with 100 ml of diisopropyl ether. After suctioning off and drying, the substance is dissolved in 40 ml of water and 24 ml of 0.1 N sodium hydroxide solution. It is stirred for 2 hours at room temperature and the solution is evaporated in a vacuum to dryness. The residue is mixed with 10 ml of isopropanol, suctioned off, washed with isopropanol and dried at 60° C. in a vacuum. 2.85 g (=86% of theory) is obtained as a white powder with a decomposition point above 250° C.

Analysis (relative to an anhydrous substance):
C 39.28, H 4.76, N 10.18 (calculated).
C 39.11, H 5.01, N 10.23 (found).

(4) $N^3$,$N^6$-bis (carboxymethyl)-$N^9$ [3,3-bis(dihydroxyphosphoryl)-3-hydroxypropylcarbamoylmethyl]-3,6,9-triazaundecanedioic acid.

2.35 g (10 mmol) of 3-amino-1-hydroxypropane-1,1-diphosphonic acid, produced according to DE 2,943,498, is suspended in 200 ml of water and mixed with 20 ml of n sodium hydroxide solution to pH9. Then, while keeping the pH constant, 12.10 g (30 mmol) of $N^3$-(2,6-dioxomorpholinoethyl)-$N^6$-(ethoxycarbonylmethyl)-3,6-diazao ctanedioic acid is added and it is stirred overnight. Then the solution is brought to a pH of 12.5 with n sodium hydroxide solution and further stirred for 3 hours. After addition of cation exchanger IR 120 to pH 7, the solution is filtered and chromatographed on silica gel (mobile solvent: butanol/ammonia/ethanol/water =5/2/1/1). The combined substance-containing eluates are evaporated in a vacuum to dryness. 1.3 g of a white powder with a melting point of 145° C. is obtained.

Analysis (relative to an anhydrous substance):
C 33.45, H 5.28, N 9.18, P 10.15 (calculated).
C 33.56, H 5.50, N 9.30, P 10.02 (found)

(5) Calcium-trisodium salt of DTPA ($CaNa_3DTPA$)

196.6 g (0.5 mol) of DTPA is refluxed with 50 g (0.5 mol) of calcium carbonate in 800 ml of water until gas generation is finished. Then, by adding 750 ml of a 2 N sodium hydroxide solution, a neutral saline solution (pH 7.1) is produced that is evaporated in a vacuum to dryness. After drying overnight in a vacuum, 246.2 g of the complex salt is obtained as monohydrate with a melting point near 178-180° C.

Analysis (relative to an anhydrous substance):
C 35.45, H 3.82, N 8.86, Ca 8.45 (calculated).
C 35.30, H 3.96, N 8.80, Ca 8.39 (found).

Pharmacological Studies

In pharmacological tests it was established that, despite an absolute and relatively low dosage, an added portion of free complexing agents or of a weaker metal complex very significantly promoted the complete elimination of the heavy metal ion.

Thus, Table 1 shows that by adding only 10% of calcium trisodium DTPA to the contrast medium, the portion of gadolinium remaining in the bodies of rats one week after i.v. injection of GdDTPA is reduced by greater than 30%, the concentration in the bones by even about 45%.

TABLE 1

$^{153}Gd$ in the rat 7 days after i.v. injection as GdDTPA/-dimeglumine in a dose of 0.1 mmol/kg, n = 3, average ± standard deviation

|  | Formulation A<br>0.1 mmol GdDTPA/<br>kg KG | Formulation B<br>0.1 mmol GdDTPA + 0.01<br>mmol $CaNa_3DTPA$/kg KG |
| --- | --- | --- |
| Bones (nmol/g) | 1.46 ± 0.21 | 0.79 ± 0.22 |
| Amount in the whole animal (% of the dose) | 0.99 ± 0.24 | 0.68 ± 0.09 |

The values in Table 2 show that adding only 2 mol % of free DTPA (formulation B) to a contrast medium based on GdDTPA reduces the gadolinium concentration in the liver of rats by more than 50% in contrast to a control with 0.08 mol % of free DTPA (formulation A) up to the 28th day after injection.

TABLE 2

$^{153}Gd$ in the liver of the rat after i.v. injection of GdDTPA/dimeglumine in a dose of 0.5 mmol/kg; mmol/g net weight of tissue; n = 3; average ± standard deviation.

|  | 2h | 6h | 1d | 3d | 7d | 14d | 28d p. inj. |
| --- | --- | --- | --- | --- | --- | --- | --- |
| Formulation A |  |  |  |  |  |  |  |
| 0.5 mmol GdDTPA + 0.0004 mmol DTPA/kg | 20<br>±2 | 20<br>±3 | 10<br>±3 | 5.6<br>±0.9 | 2.3<br>±0.6 | 1.1<br>±0.3 | 0.4<br>±0.1 |
| Formulation B |  |  |  |  |  |  |  |
| 0.5 mmol GdDTPA + 0.01 mmol DTPA/kg | 22<br>±7 | 17<br>±1 | 10<br>±2 | 5.2<br>±1.4 | 1.6<br>±0.1 | 0.6<br>±0.2 | 0.13<br>±0.01 |

This observed effect of the addition of complexing agents or of a weak metal complex to pharmaceutical preparations based on metal complexes was in no way predictable; in fact, it contradicts corresponding invitro determinations.

An assessment of the in-vivo situation is made practically impossible by the fact that all forms of the complexing agent can interact with ions produced in the body and, on the other hand, offer numerous and in places extremely stable bonding points (proteins; natural complexing agents; anions that form very slightly soluble salts) for heavy metals. In addition, to achieve the object of making available better tolerated diagnostic media, one prejudice of the man of the art had to be overcome: previously, in the production of contrast media based on metal complexes, careful attention was always paid to the fact that there was no excess of either metal ions or free complexing agents or a weaker complex in the solution, since it is known that the free complexing agents and the weaker complexes of the complexing agents with metal ions such as $Ca^{2+}$ are less well tolerated than the stronger complexes with the heavy metal ions suitable for diagnostics or therapy.

A surprise of the present invention thus also is in the extraordinarily strong effect of the addition of free complexing agents or of weak complexes to the metal complex provided for use, e.g., on human beings with reference to the stability of the bond of the metal and thus its detoxification and elimination. This advantage is, in view of the very slow elimination of heavy metals and their inherent toxicity, of such great significance that for this reason a somewhat reduced acute tolerance of a preparation can possibly be accepted.

To achieve the desired object, very low concentrations and dosages are typically sufficient. There is an upper limit on the dosage of the complexing agent or of the weaker complexes due to their acute tolerance. A range between 0.01 and 50 mol % (based on the amount of the actual diagnostically or otherwise effective complexing agent) or max. 250 mmol/l of the actual diagnostically or otherwise effective complexing agent is suitable. These amounts preferably are between 0.1 and 10 mol % or max. 50 mmol/l. These values refer to the total amounts of these additives where mixtures are used.

In no case is it necessary to add the complexing agent or weaker complex to the preparations in such a high dose that a relevant reduction in the tolerance of the final preparation occurs compared with the originally selected diagnostically or therapeutically effective metal complex. Further, there is absolutely no necessity for an isolated or even repeated administration of the complexing agent or weak complex.

The production of the drug according to the invention occurs in a known way, e.g., as disclosed in the documents cited above, by — optionally with the addition of additives common in galenic medicine — mixing the complex compounds suspended or dissolved in an aqueous medium with the complexing or weak metal complex(es) used as additive and then optionally sterilizing the suspension or solution. Suitable additives are, for example, physiologically safe buffers (e.g., tromethamine), viscosity-enhancing additives, those that increase the osmolality or, if necessary, electrolytes such as sodium chloride or, if necessary, antioxidants such as ascorbic acid.

If suspensions or solutions of the media according to the invention in water or of physiological saline solutions are desired for enteral administration or for other purposes, the media can be mixed with auxiliary agents (e.g., methyl cellulose, lactose, mannitol) and/or surfactants (e.g., lecithin, Tweens(®), Myrj(®)) and/or aromatics common in galenic medicine for flavoring (e.g., ethereal oils).

If suspensions of the complex compounds in water or a physiological saline solution are desired for oral administration or other purposes, a slightly soluble complex compound is mixed with one or more auxiliary agents and/or surfactants and/or aromatics common in galenic medicine for flavoring.

The drugs according to the invention preferably contain between 1 micromol and 1 mol/l of the diagnostically or therapeutically effective complex salt and are generally dosed in amounts between 0.001 and 5 mmol/kg. They are intended for enteral and parenteral application.

They are used in accordance with the conventional use of the underlying diagnostic or therapeutic complexes themselves, e.g., as disclosed in the documents cited above. The additives preferably are co-administered in a single formulation along with the diagnostic or therapeutic agents but could also be administered in a separate formulation administered at essentially the same time as the formulation of the active complex or sequentially.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLE 1

Production of a solution of the di-N-methylglucamine salt of the gadolinium(III)-complex of diethylenetriaminepentaacetic acid (DTPA) with the calcium trisodium salt of DTPA as additive.

97.6 g (0.5 mol) of N-methylglucamine is dissolved sterile in 50 ml of water. After the addition of 196.6 g (0.5 mol) of DTPA and 90.6 g (0.25 mol) of gadolinium oxide, $Gd_2O_3$, it is refluxed for 2 hours and the clear solution is brought to pH 7.2 by adding another 97.6 g (0.5 mol) of N-methylglucamine. Next, 24.62 g (50 mmol) of the monohydrate of the calcium trisodium salt of DTPA, $CaNa_3$ DTPA is added and water is added sterile to produce 1000 ml. The solution is ultrafiltered, placed in an ampule and heat sterilized and is ready for parenteral use.

EXAMPLE 2

Production of a solution of the di-N-methylglucamine salt of the gadolinium(III) complex of diethylenetriaminepentaacetic acid (DTPA) with the penta-N-methylglucamine salt of DTPA as additive.

97.6 g (0.5 mol) of N-methylglucamine is dissolved sterile in 500 ml of water. After addition of 196.6 g (0.5 mol) of DTPA and 90.6 g (0.25 mol) of gadolinium oxide, $Gd_2O_3$, the batch is refluxed for 2 hours and the clear solution is brought to pH 7.2 by adding another 97.6 g (0.5 mol) of N-methylglucamine. Next, another solution of 197 mg (0.5 mmol) of DTPA and 488 mg (2.5 mmol) of N-methylglucamine in 100 ml of water is added sterile and water is added sterile to produce 1000 ml. The solution is finally ultrafiltered, placed in an ampule and heat sterilized, and is ready for parenteral use.

EXAMPLE 3

Production of a solution of the sodium salt of the gadolinium(III) complex of 1,4,7,10-tetraazacyclododecane-N,N',N'''-tetraacetic acid (DOTA) with the calcium disodium salt of DOTA as additive.

290.3 g (0.5 mol) of the complex salt described in example 11 of DE 3401052 is dissolved sterile in 700 ml of water. After addition of 7.44 g (30 mmol) of the calcium disodium salt of DOTA, water is added sterile to the neutral solution to produce 1000 ml, it is ultrafiltered, placed in an ampule and heat sterilized.

EXAMPLE 4

Production of a solution of the lysine salt of the gadolinium(III) complex of DOTA with the zinc disodium salt of DOTA as additive.

80.80 g (0.2 mol) of DOTA (Parish Chemical Comp.) is introduced sterile into a suspension of 36.26 g (0.1 mol) of gadolinium oxide, $Gd_2O_3$, in 700 ml of water. It is heated with stirring for 20 hours to 70° C. and the solution is neutralized by adding an aqueous 20% by weight solution of lysine. Then 10.24 g (20 mmol) of the zinc disodium salt of DOTA is added and water is added sterile to the solution to produce 1000 ml. The solution is ultrafiltered, placed in an ampule and heat sterilized.

EXAMPLE 5

Production of a solution of the di-N-methylglucamine salt of the gadolinium(III) complex of DTPA with the calcium trisodium salt of DTPA as additive.

97.6 g (0.5 mol) of N-methylglucamine is dissolved in 20 l of water. After addition of 196.6 g (0.5 mol) of DTPA and 90.6 g (0.25 mol) of gadolinium oxide $Gd_2O_3$, it is refluxed for 5 hours. 475.4 g (1 mol) of calcium trisodium DTPA, 750 g of mannitol and 100 g of trisodium citrate is added, the solution is neutralized with N-methylglucamine and water is added to produce 50 l. The solution is poured into bottles for enteral application.

EXAMPLE 6

Production of a solution of the gadolinium(III) complex of $N^6$-carboxymethyl-$N^3$,$N^9$-bis(methylcarbamoylmethyl)-3,6,9-triazaundecanedioic acid with the N-methylglucamine sale of $N^6$-carboxymethyl-$N^3,N^9$-bis(-methylcarbamoylmethyl)-3,6,9triazaundecanedioic acid as additive.

12.58 g (30 mmol) of $N^6$-carboxymethyl-$N^3,N^9$-bis-(methylcarbamoylmethyl)-3,6,9-triazaundecanedioic acid is reacted with 5.44 g (15 mol) of gadolinium oxide, $Gd_2O_3$, in 500 ml of water for 6 hours at 90° C. 12.58 g (30 mmol) of $N^6$-carboxymethyl-$N^3,N^9$-bis(methylcarbamoylmethyl)-3,6,9-triazaundecanedioic acid, 50 g of mannitol and 8 g of trisodium citrate is added, the solution is neturalized with N-methylglucamine and water is added to produce 1000 ml. The solution is poured into bottles for enteral use.

EXAMPLE 7

Production of a solution of the di-N-methylglucamine salt of the gadolinium(III) complex of $N^6$-carboxymethyl-$N^3N^9$-bis(3-oxapentamethylenecarbamoylmethyl)-3,6,9-tr iazaundecanedioic acid, with the tetrasodium salt of $N^3,N^6$-bis-(carboxymethyl)-$N^9$-3-oxapentamethylene-carbamoylmethyl-3,6,9-triazaundecanedioic acid as additive. 17.90 g (50 mmol) of 1,5-bis-(2,6-dioxomorpholino)-3-azapentane-9-acetic acid is suspended in 150 ml of water and dissolved by adding 13.08 ml (150 mmol) of morpholine. It is stirred for 16 hours at room temperature and mixed with 16,57 (50 mmol) of gadolinium(III)-acetate dissolved in 150 ml of water. It is further stirred for 2 hours and the solution is treated successively with the anion exchanger IRA 410 and with the cation exchanger IRC 50. The neutral solution is then evaporated in a vacuum to dryness. 22.25 g (32.4 mmol) of the desired complex compound is obtained which is dissolved sterile in a solution of 12.65 g (64.8 mmol) of N-methylglucamine in 60 ml of water. 1.66 g (3 mmol) of the tetrasodium salt of $N^3,N^6$-bis-(carboxymethyl)-$N^9$-3- oxapentamethylene-carbamoylmethyl-3,6,9-triazaunde canedioic acid is added and water is added sterile to produce 100 ml. The neutral solution is ultrafiltered, placed in ampules and heat sterilized: it is ready for parenteral use.

EXAMPLE 8

Production of a solution of the disodium salt of the manganese(II) complex of trans-1,2-cyclohexylenediaminetetraacetic acid with trans-1,2-cyclohexylenediaminetetraacetic acid as additive.

395.9 g (500 mmol) of the salt described in example of DE 3401052 is suspended sterile in 500 ml of water while being exposed to nitrogen gas. It is mixed with 1.73 g of ascorbic acid and 17.3 g (50 mmol) of trans-1,2-cyclohexylenediaminetetraacetic acid, then it is neutralized by adding n sodium hydroxide solution and water is added sterile to produce 1000 ml. The solution is filtered sterile using nitrogen and poured into ampules.

EXAMPLE 9

Production of a solution of the N-methylglucamine salt of the iron(III) complex of ethylenediamine-N,N'-bis (2-hydroxyphenylacetic acid) (EHPG) with EHPG as additive.

36.04 g (0.1 mol) of EHPG is refluxed sterile in 500 ml of water with 15.97 g (0.1 mol) of iron(III) oxide, $Fe_2O_3$, until a solution has occurred. 3.604 g (0.01 mol) of EHPG is added and it is brought to pH 7.5 by adding N-methylglucamine. Water is added sterile to produce 1000 ml and the solution is ultrafiltered, poured into ampules and heat sterilized.

EXAMPLE 10

Production of an injection solution of the sodium salt of the gadolinium(III) complex of $N^3,N^6$-bis(carboxymethyl)-$N^9$[3,3-bis(dihydroxyphosphoryl)-3-hydroxypr oprylcarbamoylmethyl] -3,6,9-triazaundecanedioic acid, with $N^3,N^6$-bis(carboxymethyl)-$N^9$[3,3-bis(dihydroxyphosphoryl)-3-hydroxypropylcarbamoylmethyl] -3,6,9 -triazaundecanedioic acid as additive.

305.2 g (0.5 mol) of $N^3,N^6$-bis(carboxymethyl)-$N^9$-[3,3-bis(dihydroxyphosphoryl)3-hydroxypropyl carbamoylmethyl] -3,6,9-triazaundecanedioic acid is dissolved sterile in 8.5 l of water with addition of 123.6 g (0.25 mol) of gadolinium carbonate, $Gd_2(CO_3)_3$ at 50° C. Then another 30.52 g (0.05 mol) of the complexing agent is added and the pH is brought to 7.2 during exposure to nitrogen gas by instilling 5 n sodium hydroxide solution. Water is added sterile to the solution to produce 10 l, it is ultrafiltered, poured into ampules and heat sterilized.

EXAMPLE 11

Production of a solution of the gadolinium(III) complex from the conjugate of DTPA with a monoclonal antibody with the calcium disodium salt of DTPA as additive.

To 20 microliters of a solution of 0.3 mg of monoclonal antibody 12 H 12 in 0.05 molar sodium bicarbonate buffer, 1 mg of $N^3$-(2,6-dioxomorpholinoethyl)-$N^6$-(ethoxycarbonylmethyl)-3,6-diazaoctanedioic acid is added. After stirring overnight, it is mixed with 2 mg of gadolinium chloride, $GdCl_3$, and the solution is dialyzed through a 0.3 molar sodium phosphate buffer. Then 1 mg of the calcium trisodium salt of DTPA is added. The sterile filtered solution is poured into Multivials and lyophilized.

EXAMPLE 12

Production of a solution of the gadolinium(III) complex of the dextran-DTPA conjugate with the calcium disodium salt of EDTA as additive.

A solution of 6.5 g of dextran 10000 is brought to pH 11 with n sodium hydroxide solution. Then 2.12 g of bromocyanogen is added and it is stirred for 30 minutes, and the pH is kept constant by adding more lye. After addition of 20 g of 1-(4-aminobenzyl)DTPA, produced according to Can.Pat. 1178951, the solution is further stirred overnight at pH 8.5. Then a solution of 8 g of gadolinium chloride, $GdCl_3$, in 30 ml of water is instilled, the solution is clarified over activated carbon and dialyzed. The dialyzate is mixed with 3 g of the calcium disodium salt of ethylenediaminetetraacetic acid (EDTA), filtered sterile, poured into Multivials and lyophilized. The lyophilizate contains about 10% of complex bonded gadolinium.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising a diagnostically effective amount of the gadolinium chelate complex of N⁶-carboxymethyl-N³,N⁹-bis(methylcarbamoyl-methyl)-3,6,9-triazaundecanedioic acid, a pharmaceutically acceptable carrier and 2-10 mole % of a sodium salt of a calcium chelate complex, based on the amount of said gadolinium chelate complex, up to a maximum of 50 mmol/l of said composition, wherein said amount of calcium chelate complex is effective to enhance the safety in a human of said composition with respect to an identical composition except lacking said calcium chelate complex.

2. A composition of claim 1, wherein the amount of said sodium salt of a calcium chelate complex is 2-6 mole %.

3. A composition of claim 1 which is sterile.

4. A composition of claim 1, wherein said amount of sodium salt of a calcium chelate complex is up to a maxium of 30 mmol/l of said composition.

5. A composition of claim 1, wherein the amount of said gadolinium complex is between 1 micromole and 1 mole per liter.

6. A composition of claim 1, wherein the chelating agent of said sodium salt of a calcium chelate complex is the same as that of said gadolinium chelate complex.

7. A composition of claim 1, wherein the chelating agent of said sodium salt of a calcium chelate complex is different from that of said gadolinium chelate complex.

8. A method of obtaining an NMR image, comprising administering to a patient, of whom said image is to be obtained, a diagnostically effective amount of a pharmaceutical composition comprising a diagnostically effective amount of the gadolinium chelate complex of N⁶ carboxymethyl-N³,N⁹-bis(methylcarbamoylmethyl)3,6,9-troazaimdecamedopoc acid, a pharmaceutically acceptable carrier and 2-10 mole % of a sodium salt of a calcium chelate complex, based on the amount of said gadolinium chelate complex, up to a maximum of 50 mmol/l of said composition, wherein said amount of calcium chelate complex is effective to enhance the safety in a human of said composition with respect to an identical composition except lacking said calcium chelate complex, and taking said image.

9. A method of claim 8, wherein the amount of said sodium salt of a calcium chelate complex is 2-6 mole %.

10. A method of claim 8, wherein said composition is sterile.

11. A method of claim 8, wherein said amount of sodium salt of a calcium chelate complex is up to a maximum of 30 mmol/l of said composition.

12. A method of claim 8, wherein said amount of said gadolinium complex in said composition is between 1 micromole and 1 mole per liter.

13. A method of claim 8, wherein the chelating agent of said sodium salt of a calcium chelate complex is the same as that of said gadolinium chelate complex.

14. A method of claim 8, wherein the chelating agent of said sodium salt of a calcium chelate complex is different from that of said gadolinium chelate complex.

15. A method of claim 8, wherein the amount of the gadolinium chelate complex administered is between 0.001 and 5 mmol/kg.

16. A method of obtaining an X-ray image, comprising administering to a patient, of whom said image is to be obtained, a diagnostically effective amount of a pharmaceutical composition comprising a diagnostically effective amount of the gadolinium chelate complex of N⁶ carboxymethyl-N³,N⁹-bis(methylcarbamoylmethyl)-3,6,9-triazaundecanedioic acid, a pharmaceutically acceptable carrier and 2-10 mole % of a sodium salt of a calcium chelate complex, based on the amount of said gadolinium chelate complex, up to a maximum of 50 mmol/l of said composition, wherein said amount of calcium chelate complex is effective to enhance the safety in a human of said composition with respect to an identical composition except lacking said calcium chelate complex, and taking said image.

17. A method of claim 16, wherein the amount of said sodium salt of a calcium chelate complex is 2-6 mole %.

18. A method of claim 16, wherein said composition is sterile.

19. A method of claim 16, wherein said amount of sodium salt of a calcium chelate complex is up to a maximum of 30 mmol/l of said composition.

20. A method of claim 16, wherein the amount of said gadolinium complex in said composition is between 1 micromole and 1 mole per liter.

21. A composition of claim 16, wherein the chelating agent of said sodium salt of a calcium chelate complex is the same as that of said gadolinium chelate complex.

22. A method of claim 16, wherein the chelating agent of said sodium salt of a calcium chelate complex is different from that of said gadolinium chelate complex.

23. A method of claim 16, wherein the amount of the gadolinium chelate complex administered is between 0.001 and 5 mmol/kg.

24. A composition of claim 1, wherein said amount of sodium salt of a calcium chelate complex is 2-6 mole % based on the amount of said gadolinium chelate complex and is up to a maximum of 30 mmol/l of said composition, and wherein the chelating agent of said sodium salt of a calcium chelate complex is the same as that of said gadolinium chelate complex.

25. A method of claim 8, wherein said amount of sodium salt of a calcium chelate complex is 2-6 mole % based on the amount of said gadolinium chelate complex and is up to a maximum of 30 mmol/l of said composition, and wherein the chelating agent of said sodium salt of a calcium chelate complex is the same as that of said gadolinium chelate complex.

* * * * *

UNITED STATES PATENT AND TRADEMARK OFFICE
CERTIFICATE OF CORRECTION

PATENT NO. : 5,098,692
DATED : March 24, 1992
INVENTOR(S) : Heinz GRIES et al.

It is certified that error appears in the above-identified patent and that said Letters Patent is hereby corrected as shown below:

Claim 8; Col. 11; Line 34 - - -

Reads thyl)3,6,9, troazaimdecamedopoc acid

Should read ;

thyl)-3,6,9-triazaundecanedioic acid,

Signed and Sealed this

Sixth Day of July, 1993

Attest:

MICHAEL K. KIRK

Attesting Officer     Acting Commissioner of Patents and Trademarks